US008759034B2

(12) United States Patent
Montilla Arevalo et al.

(10) Patent No.: US 8,759,034 B2
(45) Date of Patent: *Jun. 24, 2014

(54) THERMOSTABLE BIOCATALYST COMBINATION FOR NUCLEOSIDE SYNTHESIS

(71) Applicant: Plasmia Biotech, S.L., Mollet del Vallès (ES)

(72) Inventors: Rafael Montilla Arevalo, Mollet del Vallès (ES); Victor Manuel DeronceléThomas, Mollet del Vallès (ES); Cristina López Gómez, Mollet del Vallès (ES); Marta Pascual Gilabert, Mollet del Vallès (ES); Carlos Estevez Company, Mollet del Vallès (ES); Josep Castells Boliart, Mollet del Vallès (ES)

(73) Assignee: Plasmia Biotech, S.L., Mollet del Valles (ES)

( * ) Notice: Subject to any disclaimer, the term of this patent is extended or adjusted under 35 U.S.C. 154(b) by 0 days.

This patent is subject to a terminal disclaimer.

(21) Appl. No.: 13/947,621

(22) Filed: Jul. 22, 2013

(65) Prior Publication Data
US 2013/0337547 A1    Dec. 19, 2013

Related U.S. Application Data

(63) Continuation of application No. 13/518,068, filed as application No. PCT/EP2010/070581 on Dec. 22, 2010, now Pat. No. 8,512,997.

(30) Foreign Application Priority Data

Dec. 22, 2009    (EP) .................... 09382296

(51) Int. Cl.
*C12N 9/22*    (2006.01)
(52) U.S. Cl.
USPC ........................ 435/88; 435/252.3
(58) Field of Classification Search
CPC ............... C12N 15/111; C12N 15/113; C12N 2310/14; C12N 2310/53; C12N 2330/30; C12N 9/22
USPC .................................... 435/252.33
See application file for complete search history.

(56) References Cited

U.S. PATENT DOCUMENTS

2005/0142645 A1    6/2005    Bestetti et al.

FOREIGN PATENT DOCUMENTS

| EP | 1141328 A2 | 10/2001 |
| JP | 06-253854 A | 9/1994 |
| WO | WO-95/16785 A1 | 6/1995 |
| WO | WO-00/39307 A2 | 7/2000 |
| WO | WO-03/035012 A2 | 5/2003 |

OTHER PUBLICATIONS

Madruga, Jamie, "International Search Report" for PCT/EP2010/070581 as mailed Jun. 1, 2011, 9 pages.
Taran, S.A., et al., "Enzymatic transglycosylation of natural and modified nucleosides by immobilized thermostable nucleoside phosphorylases from *Geobacillus stearothermophilus*", Russian Journal of Bioorganic Chemistry, vol. 35, No. 6, Nov. 2009, pp. 739-745.
Trelles, J.A., et al., "Screening of Catalytically Active Microorganisms for the Synthesis of 6-Modified Purine Nucleosides", Biotechnology Letters, Kluwer Academic Publishers, vol. 27, No. 11, Jun. 1, 2005, pp. 759-763.
Database Uniprot [Online], Nov. 1, 1999, "SubName: Full=Uridine phosphorylase; EC=<A HREF="http://srs.ebi.ac.uk/srsbin/cgi-bin/wgetz?    [enzyme-ECNumber:2.4.2.3]+-e>2.4.2.3</A>;    , XP002585195, retrieved from EBI accession No. UNIPROT:Q9YA34.
Hamamoto, Tomoki, et al., "Cloning of purine nucleoside phosphorylase II gene from *Bacillus stearothermophilus* TH 6-2 and characterization of its gene product", Bioscience Biotechnology and Biochemistry, vol. 61, No. 2, 1997, pp. 276-280.
Hamamoto, Tomoki, et al., "Cloning and expression of purine nucleoside phosphorylase I gene from *Bicillus stearothermophilus* TH 6-2", Bioscience Biotechnology and Biochemistry, vol. 61, No. 2, 1997, pp. 272-275.
Cacciapuoti, Giovanna, et al., "Purine nucleoside phosphorylases from hyperthermophilic Archaea require a CXC motif for stability and folding", The FEBS Journal, Oct. 2009, vol. 276, No. 20, pp. 5799-5805.
Cacciapuoti, Giovanna, et al., "A novel hyperthermostable 5'-deoxy-5'-methylthioadenosine phosphorylase from the archaeon *Sulfolobus solfataricus*", FEBS Journal, vol. 272, No. 8, Apr. 2005, pp. 1886-1899.
Cacciapuoti, Giovanna, et al., "Biochemical and structural characterization of mammalian-like purine nucleoside phosphorylase from the Archaeon Pyrococcus Furiosus", FEBS Journal, vol. 274, No. 10, May 2007, pp. 2482-2495.
She, Qunxin, et al., "The complete genome of the crenarchaeon *Sulfolobus solfataricus* P2", Proceedings of the National Academy of Sciences of the United States of America, vol. 98, No. 14, Jul. 3, 2001, pp. 7835-7840.

(Continued)

*Primary Examiner* — Tekchand Saidha
*Assistant Examiner* — Rama P Ramanujam
(74) *Attorney, Agent, or Firm* — Winstead PC

(57) ABSTRACT

A recombinant expression vector comprising: a) the sequence encoding a purine nucleoside phosphorylase (PNPase, E. C. 2.4.2.1), b) the sequence encoding a uridine phosphorylase (UPase, E. C. 2.4.2.3), c) or both; each of the sequences operably linked to one or more control sequences that direct the production of said phosphorylases in a suitable expression host; said sequences originating from the Archaea Thermoprotei class, characterized in that the PNPase is from *Sulfolobus solfataricus* (SEQ ID NO. 7) and the UPase is from *Aeropyrum pernix* (SEQ ID NO. 8). In addition, the present invention relates to A transglycosylation method between a sugar-donating nucleoside and an acceptor base in the presence of phosphate ions, characterized in that said method comprises the use of a uridine phosphorylase (UPase) of *Aeropyrum pernix* (NC_000854.2), a purine nucleoside phosphorylase (PNpase) of *Sulfolobus solfataricus* (NC_002754.1), or a combination thereof.

4 Claims, 6 Drawing Sheets

(56) References Cited

OTHER PUBLICATIONS

Cacciapuoti, Giovanna, et al., "Purification and characterization of extremely thermophilic and thermostable 5'-methylthioadenosine phosphorylase from the archaeon *Sulfolobus solfataricus*: Purine nucleoside phosphorylase activity and evidence for intersubunit disulfide bonds", Journal of Biological Chemistry, vol. 269, No. 40, 1994, pp. 24762-24769.

Cacciapuoti, Giovanna, et al., "Extremely thermophilic and thermostable 5'-methylthioadenosine phosphorylase from the archaeon *Sulfolobus solfataricus*: Gene cloning and amino acid sequence determination", European Journal of Biochemistry, vol. 239, No. 3, 1996, pp. 632-637.

Kawarabayasi, Yutaka, et al., "Complete Genome Sequence of an Aerobic Hyper-thermophilic Crenarchaeon, *Aeropyrum pernix K1*", DNA Research 6, 83-101 (1999).

Fujiwara, Shinsuke, et al., Unusual enzyme characteristics of aspartyl-tRNA synthetase from hyperthermophilic archaeon *Pyrococcus* sp. KOD1, FEBS Letters 394, 66-70, (1996).

Bzowska, Agnieszka, et al., "Purine nucleoside phosphorylases: properties, functions, and clinical aspects", Pharmacology & Therapeutics 88, 349-425 (2000).

Yu, Xue-Jun, et al., "Stereoselective synthesis of 9-β-$_D$-arabianofuranosyl guanine and 2-amino-9-((β-$_D$-arabianofuranosyl)purine", Bioorganic & Medicinal Chemistry Letters 15, 683-685, (2005).

Brown, Stephen H., et al., "Characterization of Amylolytic Enzymes, Having Both α-1,4 and α-1,6 Hydrolytic Activity, from the Thermophilic Archaea *Pyrococcus furiosus* and *Thermococcus litoralis*", Applied and Environmental Microbiology, 2614-2621, Aug. 1993.

Retrieved from EBI accession No. UNIPROT: Q97Y30, "SubName: Full=Purine nucleoside phosporylase (DeoD)", XP-002625014, Oct. 1, 2001.

Purcarea, Cristina, et al., "Purification and characterization of carbamoyl-phosphate synthetase from the deep-sea hyperthermophilic archaebacterium *Pyrococcus abyssi*", Eur. J. Biochem, 236, 189-199, (1996).

Saunders, P.P., et al., "Purification and Comparative Properties of a Pyrimidine Nucleoside Phosphorylase from *Bacillus stearothermophilus*", The Journal of Biological Chemistry, vol. 244, No. 13, Issue of Jul. 10, 3691-3697, (1969).

Hutchinson, David W., "New approaches to the synthesis of antiviral nucleosides", TIBTECH—Dec. 1990 (vol. 8), 348-353.

Van Rompay, An R., et al, "Substrate specificity and phosphorylation of antiviral and anticancer nucleoside analogues by human deoxyribonucleoside kinases and ribonucleoside kinases", Pharmacology & Therapeutics 100,119-139, (2003).

Cacciapuoti, Giovanna, et al., "Heterologous Expression of 5'-Methylthioadenosine Phosphorylase from the Archaeon *Sulfolobus solfataricus*: Characterization of the Recombinant Protein and Involvement of Disulfide Bonds in Thermophilicity and Thermostability", Protein Expression and Purificaiton 16, 125-135, (1999).

Yanisch-Perron, Celeste, et al., "Improved M13 phage cloning vectors and host strains: nucleotide sequences of the M13mp18 and pUC19 vectors", Gene, 33, 103-119, (1985).

Taran, S.A., et al., "Synthesis of 2-Chloro-2'-deoxyadenosine by Microbiological Transglycosylation Using a Recombinant *Escherichia coli* Strain", Applied Biochemistry and Microbiology, vol. 44., No. 2, 162-166, (2008).

Figure 7.

```
  1 gtgccatttt tagaaaatgg ttccatggta tatggtgatt tcattagaaa tcaagaggta
 61 agaaaaagaa ttacaaagga agaacttggg atagaagaag acgaaatccc ggaaagggta
121 gttgtaacac ctatgccatt taatactcaa tttcctaaaa actttgaaga tactttaact
181 aacttaggaa ttaaagtaaa taggttaaaa gtggaagacc aaatacttag acaattcgga
241 ggaaatttat tgcttgaaaa agacggtaat agaggattta ttgcgttcat aggcagaggt
301 ctgatagatt tcactgagag gataaggatt ttagctacag tttcgcgcat taaagatata
361 ttatttattg gtactgcagg atcgttatct aatgaaatat taataggaga tctaaatata
421 ccaaaatacg ccatcccatt cgaaaacgta agtgattttt acgctgatcc taccatagca
481 attccacaag ctgatgaaaa gttgctgaac gaagtttatg agtacgctga ggaaactgga
541 gttaaaaccc actcaaccct acatgcaaca ctactttcc cttattccga aactactgag
601 ttcctaaact acttattaaa tatcggcgtt tctacgatag atatggaagt cagtgctttt
661 tataagatgt ctagatttta cggtaaaaga gctgttgcag tattacgaat ttcagatatg
721 cctttaatag aactgcataa gcaagaggaa ttgattaagg caagaaggga aattgcagtt
781 aatgctgttt tcagaattac cttaagattc ttaaaactga tttaa
```

Figure 8

```
  1 gtggcccgct acgttctcct cccgggagac cccgagagga cagaccttat agcccgcctc
 61 tgggatgaag cgaggcttgt agcgcaccac cgggagtaca ggacgtggac cggcttctac
121 aaggggacat cgataagtgt aacaagcacc gggataggct ctcccagcac ggcgatagcc
181 gttgaggagc tgctgagggt tggagccgag actttcataa gagtaggcac tatgggcggt
241 ataagggagg atctgcggcc cggcaccctg gttataggga gtgcggcggt taggatggag
301 gggacgagcg gccagtacgc tccccggggg ttcccagcgg ccgccagcta tgacgttgtg
361 gcggcgctgg tggaggctgc tgaggcgctc ggggttaggt atgaggttgg cgttgttgcc
421 agcacggaca gcttctacct gggccagggg aggccggggt acgggggta tatgacgccg
481 gaggcttcgg aagtcatacc cctcctcagg tcagccggcg tcctcggctt cgagatggag
541 gcctccgccc tcttcacct atcccagctc tacggcgcca gggcagggtg cgtgtgcgcg
601 gtagtggcaa acagggttag cggggagttt gtggtaaacg cggggttga agacgctgct
661 agggttgcct ccgaggcggt agccatacta gcaggctggg acagggagag ggagaagagg
721 ggtaagaaat ggttttaccc gagcctggcg tgcagacgca catag
```

THERMOSTABLE BIOCATALYST COMBINATION FOR NUCLEOSIDE SYNTHESIS

This patent application is a continuation of U.S. patent application Ser. No. 13/518,068, filed on Jun. 21, 2012. U.S. patent application Ser. No. 13/518,068 is a national-stage filing of PCT/EP2010/070581, filed on Dec. 22, 2010. U.S. patent application Ser. No. 13/518,068 and PCT/EP2010/070581 are incorporated by reference herein.

FIELD OF THE INVENTION

The invention belongs to the field of biotechnology.

BACKGROUND OF THE INVENTION (Deoxy)nucleosides are glycosylamines consisting of a base like a purine or a pyrimidine bound to a ribose or deoxyribose sugar, the latter being cyclic pentoses. Examples of these include cytidine, uridine, adenosine, guanosine, thymidine, and inosine. Nucleoside analogues are extensively used as antiviral and anticancer agents because of their ability to act as reverse transcriptase inhibitors or chain terminators in RNA or DNA synthesis [1].

Chemical synthesis of nucleoside analogues has been achieved stereoselectively but using expensive or polluting reagents [2] and involving multistage processes that can be time consuming. Biocatalytic procedures offer a good alternative to the chemical synthesis of nucleosides because biocatalyzed reactions are regio- and stereoselective and allow the decrease of by-products content. Of particular interest within the biocatalytic procedures is the enzymatic transglycosylation between a sugar-donating nucleoside and an acceptor base by means of enzymes that catalyse the general reversible reactions [3] as depicted in FIGS. 1 and 2.

Nucleoside phosphorylases are transferases widely distributed in mammalian cells and bacteria and play a central role in the nucleoside metabolism salvage pathway. They have a dual functionality. On the one hand, they catalyse the reversible cleavage of the glycosidic bond of ribo- or deoxyribo nucleosides in the presence of inorganic phosphate in order to generate the base and ribose- or deoxyribose-1-phosphate. These enzymatic reactions employing the purine nucleoside phosphorylases and the pyrimidine nucleoside phosphorylases are shown in FIG. 1. On the other hand, these enzymes catalyse phosphate-dependent pentose transfer between purine or pyrimidine bases and nucleosides, i.e. transglycosylation reactions, to produce nucleosides with differing bases. FIG. 2 shows an example of a one-pot synthesis using nucleoside phosphorylases.

When the pyrimidine and purine nucleoside phosphorylases are used in combination, it is possible to transfer the sugar from a donor pyrimidine nucleoside to a purine or pyrimidine acceptor base as well as from a donor purine nucleoside to a pyrimidine or purine acceptor base, depending on the starting materials used [4]. As a consequence, nucleoside phosphorylases from different sources, mainly bacterial, have been exploited as tools for the enzymatic synthesis of nucleoside analogues.

In nature these enzymes have been described in various microbial strains, particularly in thermophilic bacteria (i.e. bacteria thriving at temperatures between 45° C. and 80° C.), which have been used as sources of nucleoside phosphorylases in numerous works for obtaining modified nucleosides by enzymatic transglycosylation. However, although in these studies the target products yields were sufficiently high, the amount or ratio of the enzymatic activities necessary for transglycosylation was non-optimal [5]. They required either a considerable extension in the reaction time (up to several days) or an increase in the used bacterial biomass to reach the necessary transformation depth.

Besides, when developing a transglycosylation process another problem arises: the difficult solubilization of large amounts of substrates and products, many of them poorly soluble in aqueous medium at room temperature. Although this problem could be solved using higher temperatures, it requires enzymes sufficiently stable in these harder reaction conditions.

The Archaea are a group of single-celled microorganisms that are one of the three domains of life; the others being Bacteria and Eukarya. They were formerly called Archaebacteria under the taxon Bacteria, but now are considered separate and distinct. The archaeal domain is currently divided into two major phyla, the Euryarchaeota and Crenarchaeota. The Euryarchaeota includes a mixture of methanogens, extreme halophiles, thermoacidophiles, and a few hyperthermophiles. By contrast, the Crenarchaeota includes only hyperthermophiles. Hyperthermophiles are those organisms that thrive in extremely hot environments, from 60° C. upwards, optimally above 80° C.

Cacciapuoti et al. [6-8] describe two purine nucleoside phosphorylases (PNPases) from hyperthermophilic Archaea, in particular it discloses the enzymes 5'-deoxy-5'-methylthioadenosine phosphorylase II (SsMTAPII, EC 2.4.2.28) from *Sulfolobus solfataricus*, and purine nucleoside phosphorylase (PfPNP) from *Pyrococcus furiosus*. The *Pyrococcus furiosus* enzyme was firstly annotated as MTAPII but renamed to PNP as it is unable to cleave methylthioadenosine. *Sulfolobus solfataricus* belongs to the Crenarchaeota, while *Pyrococcus furiosus* belongs to the Euryarchaeota. The EC code above is the conventional enzyme nomenclature provided by the International Union of Biochemistry and Molecular Biology that classifies enzymes by the reactions they catalyse.

Most enzymes characterized from hyperthermophiles are optimally active at temperatures close to the host organism's optimal growth temperature. When cloned and expressed in mesophilic hosts like *Escherichia coli*, hyperthermophilic enzymes usually retain their thermal properties. Sometimes the enzymes are optimally active at temperatures far above the host organism's optimum growth temperature [9]. Other times enzymes have been described to be optimally active at 10° C. to 20° C. below the organism's optimum growth temperature [10-11]. However, the *Sulfolobus solfataricus* 5'-methylthioadenosine phosphorylase (a hexameric enzyme containing six intersubunit disulfide bridges), when expressed in a mesophilic host, forms incorrect disulfide bridges and is less stable and less thermophilic than the native enzyme [12].

The Thermoprotei are a hyperthermophilic class of the Crenarchaeota. From the genomes sequenced and available for the Archaea Thermoprotei class, only three sequences for purine-nucleoside phosphorylase (EC 2.4.2.1) and only three sequences for uridine phosphorylase (EC 2.4.2.3), were found. These six proteins have been entered, respectively, in UniProtKB/TrEMBL with the accession numbers: A1RW90 (A1RW90_THEPD), for the hypothetical protein from *Thermofilum pendens* (strain Hrk 5); Q97Y30 (Q97Y30_SULSO), for the hypothetical protein from *Sulfolobus solfataricus*; A3DME1 (A3DME1_STAMF), for the hypothetical protein from *Staphylothermus marinus* (strain ATCC 43588/DSM 3639/F1); Q9YA34 (Q9YA34_AERPE), for the hypothetical protein from *Aeropyrum pernix*; A2BJ06 (A2BJ06_HYPBU) for the hypothetical protein from *Hyperthermus butylicus* (strain DSM 5456/JCM 9403); and D9PZN7 (D9PZN7_ACIS3) for the hypothetical protein from *Acidilobus saccharovorans* (strain DSM 16705/VKM B-2471/345-15). All these sequences were under the annotation status of unreviewed, which means that their presence in the Archaea has only been verified by computer.

Even though many genes can be successfully expressed in *Escherichia coli* at high yields, several proteins from hyperthermophiles are poorly or not at all expressed, partially due to the usage of rare codons. Indeed, and to the best of our knowledge, no party was yet successful in expressing any of the mentioned genes above.

In view of the prejudices above, in view of the technical difficulties, the inventors unexpectedly were able to prepare viable recombinant vectors and importantly, obtain recombinant phosphorylases that were optimally active at temperatures higher than 60° C. The thermostable and chemically stable catalysts of the present invention are a purine nucleoside phosphorylase (PNPase, E.C. 2.4.2.1), and a uridine phosphorylase (UPase, E.C. 2.4.2.3), originating from the Archaea Thermoprotei class, wherein the PNPase is from *Sulfolobus solfataricus* (SEQ ID NO. 7) and the UPase is from *Aeropyrum pernix* (SEQ ID NO. 8).

In particular, it has been surprisingly found that the recombinant nucleoside phosphorylases derived from the hyperthermophilic Thermoprotei have unique structure-function properties like enhanced thermostability, high catalytic efficiency, and optimal enzymatic activities at temperatures near or above 100° C. These recombinant enzymes can advantageously be used for transglycosylation reactions, in the form of cell lysate and in the form of crude or purified extracts, for industrial production of natural and modified nucleoside analogues. They are in particular versatile since they can catalyze transglycosylations in aqueous media, in organic solvents, at temperatures between 60° C. and 120° C., or in a combination of these parameters, allowing the preparation of many and diverse types of nucleosides at acceptable production yields, reaction times, and employing economical amounts of the enzymes. Importantly, the biocatalysts described in the present invention can be used for bioconversion reactions that require the presence of organic solvents, temperatures above 60° C., or both, in order to solubilize the substrates or the reaction products. These phosphorylases are ideal in reactions with water-insoluble substrates. Another advantage of these phosphorylases resides in their organic solvent tolerance, and in that they can be reused for several reaction cycles.

More advantageously, the invention offers a combination of Thermoprotei nucleoside phosphorylases that is useful for one-pot synthesis of nucleosides. The enzymes can be used to produce natural or analog nucleosides in a one-step (one-pot) or two-step synthetic methods. In the one-step synthesis, a pyrimidine nucleoside phosphorylase and a purine nucleoside phosphorylase are used in the same batch in order to change the base linked to the sugar by another one of choice. In the two step, a pyrimidine nucleoside phosphorylase is used for the liberation of the sugar of a pyrimidine nucleoside, and then, the 1-phosphate-sugar is isolated and later on, in another vessel, a purine base is linked to the sugar using a purine nucleoside phosphorylase.

SUMMARY OF THE INVENTION

The present invention relates to a recombinant expression vector comprising: a) the sequence encoding a purine nucleoside phosphorylase (PNPase, E.C. 2.4.2.1), b) the sequence encoding a uridine phosphorylase (UPase, E.C. 2.4.2.3), c) or both; each of the sequences operably linked to one or more control sequences that direct the production of said phosphorylases in a suitable expression host; said sequences originating from the Archaea Thermoprotei class, characterized in that the PNPase is from *Sulfolobus solfataricus* (SEQ ID NO. 7) and the UPase is from *Aeropyrum pernix* (SEQ ID NO. 8).

In addition, the present invention relates to A transglycosylation method between a sugar-donating nucleoside and an acceptor base in the presence of phosphate ions, characterised in that said method comprises the use of a uridine phosphorylase (UPase) of *Aeropyrum pernix* (National Center for Biotechnology Information Reference Sequence: NC_000854.2), a purine nucleoside phosphorylase (PNPase) of *Sulfolobus solfataricus* (NCBI RefSeq: NC_002754.1), or a combination thereof.

DESCRIPTION OF THE FIGURES

FIG. 7 depicts the DNA sequence (SEQ ID NO. 7) of the coding region of the purine nucleoside phosphorylase (PNPase) of *Sulfolobus solfataricus*, a.k.a. deoD gene. GenBank accession number AE006766.

FIG. 8 depicts the DNA sequence (SEQ ID NO. 8) of the coding region of the pyrimidine nucleoside phosphorylase (UPase) of *Aeropyrum pernix*, a.k.a. udp gene. GenBank accession number NC000854.

DESCRIPTION OF THE INVENTION

Figure 1:
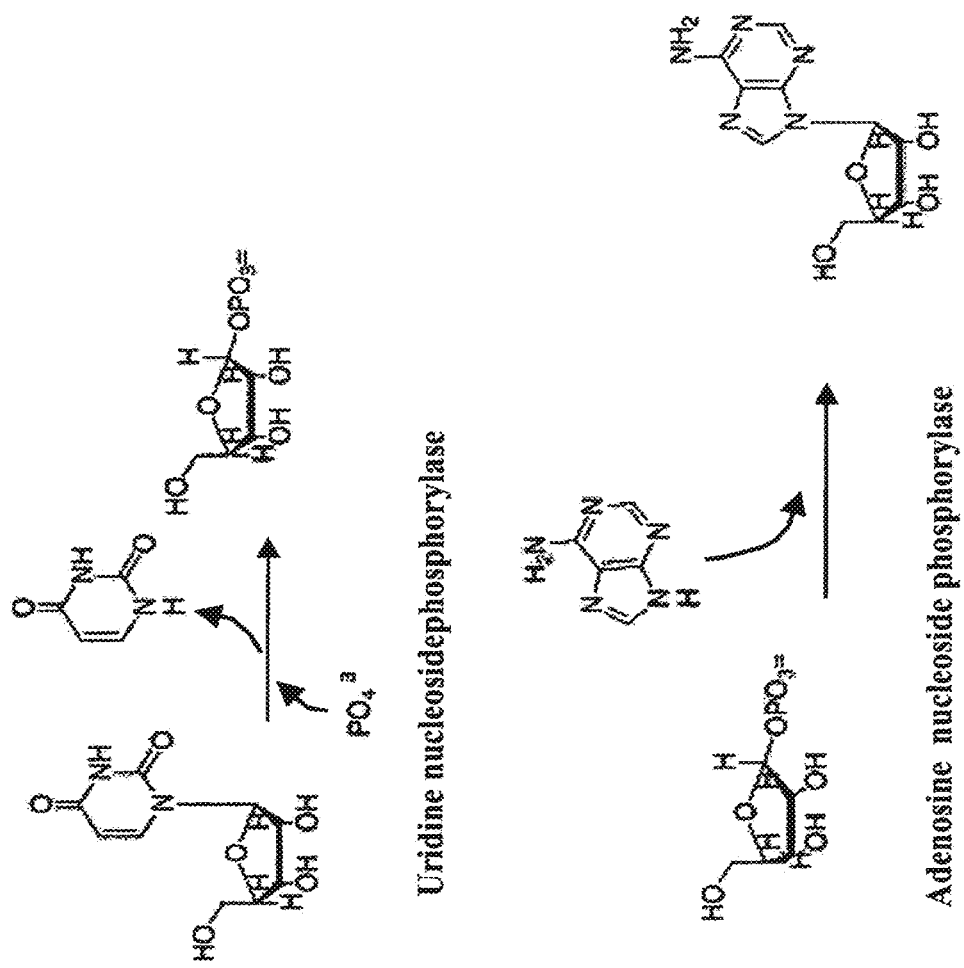
FIG. 1 shows an example of two enzymatic reactions catalyzed by nucleoside phosphorylases. The first reaction on top is a phosphorolysis that takes place through an $S_N1$-like mechanism via an oxonium-like intermediate to give α-ribose-1-phosphate. The second reaction occurs through an $S_N2$ mechanism where phosphate is substituted by a base affording the β-nucleoside [13]. In the scheme, uridine nucleoside phosphorylase catalyzes the phosphorolytic cleavage of the C—N glycosidic bond of uridine resulting in ribose-1-phosphate and uracil. The purine nucleoside phosphorylase (adenosine nucleoside phosphorylase) catalyzes the cleavage of the glycosidic bond, in the presence of inorganic orthophosphate ($P_i$) as a second substrate, to generate the purine base and ribose(deoxyribose)-1-phosphate. For the natural substrates, the reactions are reversible.
Figure 2:
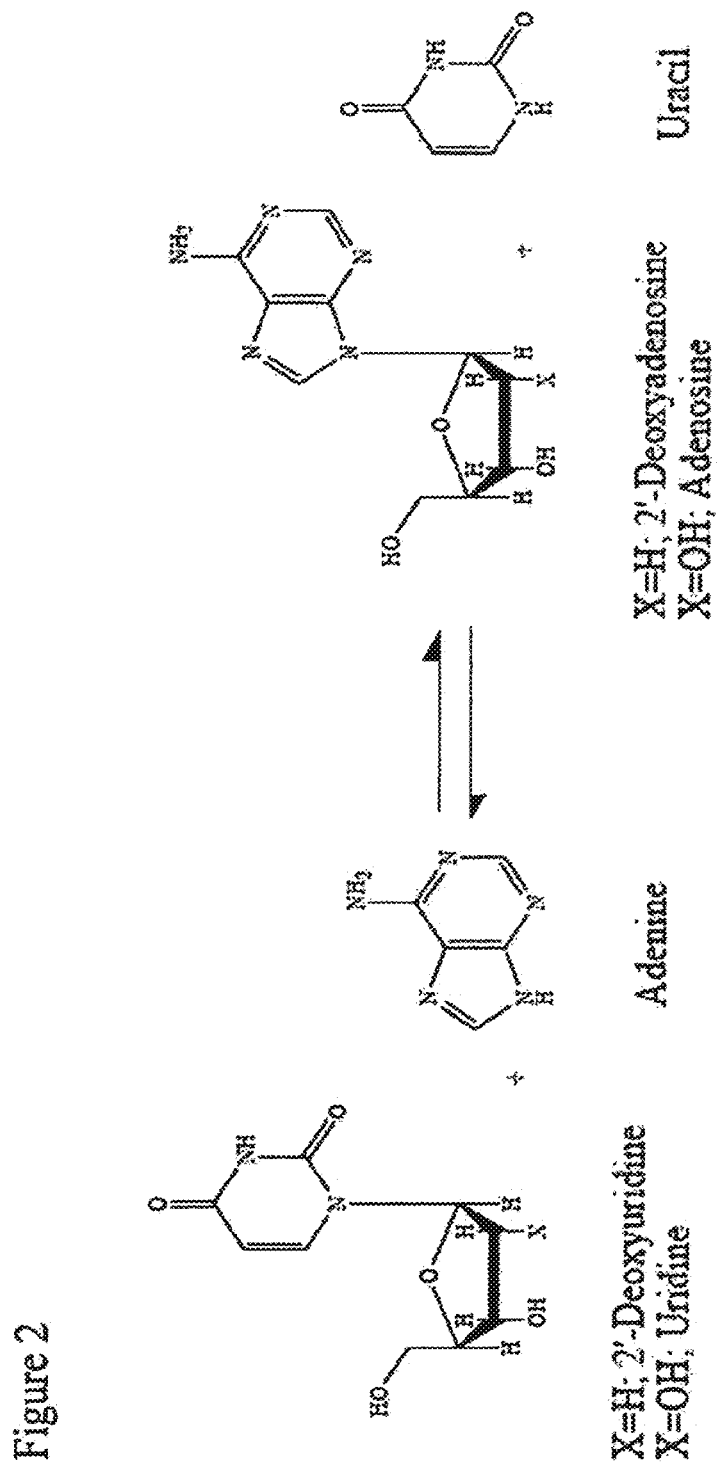
FIG. 2. Scheme of one-pot synthesis using nucleoside phosphorylase enzymes.

The present invention relates to a recombinant expression vector comprising: a) the sequence encoding a purine nucleoside phosphorylase (PNPase, E.C. 2.4.2.1), b) the sequence encoding a uridine phosphorylase (UPase, E.C. 2.4.2.3), c) or both; each of the sequences operably linked to one or more control sequences that direct the production of said phosphorylases in a suitable expression host; said sequences originating from the Archaea Thermoprotei class, characterized in that the PNPase is from *Sulfolobus solfataricus* (SEQ ID NO. 7) and the UPase is from *Aeropyrum pernix* (SEQ ID NO. 8).

*Aeropyrum pernix* and *Sulfolobus solfataricus* are hyperthermophilic Archaea capable of growing at high temperatures, over 90° C. Archaea are organisms belonging to a third group of organisms distinct from eukaryotes and prokaryotes. They are considered to descend from primeval organisms, and are special organisms which have neither evolved nor adapted to ordinary temperature environments.

UPase and PNPase in their intracellular natural environment do not allow the synthesis of nucleoside or nucleoside analogues with high yield as desired at industrial level. To overcome this serious limitation, inventors have used recombinant DNA technology to design an expression vector comprising udp and deoD genes and appropriate elements to over-express nucleoside phosphorylases in selected hosts, like bacteria. The designed expression vector also facilitates the solubilization and the purification of the different phosphorylases.

The vectors of the present invention comprise a nucleotide sequence encoding different nucleoside phosphorylases and nucleotide sequences that allow said vector to be selectable and autonomously replicable in the host cell.

The construction of the recombinant expression vector is carried out using conventional recombinant DNA technologies, i.e. procedures to join together DNA segments in a cell-free system.

The term "vector" refers to a DNA molecule originating from a virus, a plasmid, or the cell of a higher organism in which another DNA fragment of appropriate size can be integrated (cloned) without loss of the vector capacity for self-replication. Examples are plasmids, cosmids, and yeast artificial chromosomes. Vectors are often recombinant molecules containing DNA sequences from several sources. The term "expression vector" means a vector that further comprises the necessary control or regulatory sequences to allow transcription and translation of the cloned gene or genes. Circular or linearized DNA vectors are useful for this invention.

To allow the vector of the invention to be selectable and autonomously replicable in host cells, the selected vector must be compatible with the selected host cells. In a preferred embodiment, the nucleotide sequence which allows said vector to be selectable and autonomously replicable in *Escherichia coli* is the T7 promoter-encoding gene which permits the T7 RNA polymerase of the selected strain of *Escherichia coli* to bind to the promoter. The term "selectable" means that the vector remains stable in the descendent bacteria. The selection is achieved by stringent medium conditions according to the introduction of an appropriate selectable marker gene in the vector whose expression allows one to identify cells that have been transformed with the vector. The selectable marker gene is often an antibiotic-resistant gene. Preferred selectable marker genes for this invention are kanamycin, tetracycline, carbenicillin and more preferably, ampicillin.

The present invention further relates to a host cell comprising any one of the recombinant expression vectors mentioned above, or both recombinant expression vectors within the same host cell.

The term "host cell" refers to a cell transformed with the recombinant expression vector that comprises the PNPase or UPase nucleotide sequence. Another aspect of the recombinant DNA vector allows the host cell to produce nucleoside phosphorylases, and when medium conditions are suitable, said nucleoside phosphorylases catalyze the obtention of nucleosides. In a particular embodiment of the invention, PNPase and UPase genes from *Sulfolobus solfataricus* and *Aeropyrum pernix*, respectively, were introduced in the DNA expression vector. FIG. 7 and FIG. 8 list nucleic acid and amino acid sequences relevant to the invention, namely the nucleic acid sequence of *Sulfolobus solfataricus* deoD (SEQ ID NO. 7) and nucleic acid sequence of *Aeropyrum pernix* udp (SEQ ID NO. 8), respectively.

Those skilled in the art will appropriately choose the expression system constituted by an initial vector and a host cell strain to maximize the production of nucleosides.

In one embodiment, the host cell is *Escherichia coli*.

In a particular embodiment, the *Escherichia coli* belongs to BL21 bacterial strain. Suitable expression vectors for *Escherichia coli* BL21 are for instance pET vectors, trcHis vectors and pUB vectors (all of them from Invitrogen), and pGEX vectors and GST vectors (from Amersham). *Escherichia coli* DH5 alfa bacterial strain in combination with pUC vectors and *Escherichia coli* F' in combination with PSL vectors, PEZZ vectors or M13 vectors (all of them from Amersham) are also useful in this invention.

In one embodiment, the host cell is processed or is in the form of a lysate.

The present invention further relates to a transglycosylation method between a sugar-donating nucleoside and an acceptor base in the presence of phosphate ions, characterised in that said method comprises the use of a uridine phosphorylase (UPase) of *Aeropyrum pernix* (NC_000854.2), a purine nucleoside phosphorylase (PNPase) of *Sulfolobus solfataricus* (NC_002754.1), or a combination thereof.

The term "sugar-donating nucleoside" refers to a glycosylamine consisting of a nucleobase (often referred to as simply base) bound to a ribose or deoxyribose sugar via a beta-glycosidic linkage. Examples of "sugar-donating nucleosides" include, without being limited to, cytidine, uridine, adenosine, guanosine, thymidine and inosine, as well as those natural or modified nucleosides containing D-ribose or 2'-deoxyribose; nucleosides containing the ribose group modified in the 2', 3', and/or 5' positions; and nucleosides in which the sugar is beta-D-arabinose, alpha-L-xylose, 3'-deoxyribose, 3',5'-dideoxyribose, 2',3'-dideoxyribose, 5'-deoxyribose, 2',5'-dideoxyribose, 2'-amino-2'-deoxyribose, 3'-amino-3'-deoxyribose, or 2'-fluoro-2'-deoxyribose.

The term "acceptor base" refers to a nucleobase, nucleotide base, nitrogenous base, or simply base. In nature, bases are part of DNA or RNA. The primary nucleobases are cytosine, guanine, adenine (DNA and RNA), thymine (DNA) and uracil (RNA), abbreviated as C, G, A, T, and U, respectively.

The term "acceptor base" in the present invention is meant to comprise also modified and analog nucleobases. In DNA, the most common modified base is 5-methylcytidine (m5C). In RNA, there are many modified bases, including pseudouridine (Ψ), dihydrouridine (D), inosine (I), ribothymidine (rT) and 7-methylguanosine (m7G). Hypoxanthine and xanthine are two of the many bases created through mutagen presence. Other examples of acceptor bases include natural or substituted pyrimidine and purine bases; purine bases substituted at one or more of the 1, 2, 6 positions; pyrimidine bases substituted at one or more of the 3, 5 positions; and purine, 2-azapurine, 8-azapurine, 1-deazapurine (imidazopyridine), 3-deazapurine, 7-deazapurine, 2,6-diaminopurine, 5-fluorouracil, 5-trifluoromethyluracil, trans-zeatin, 2-chloro-6-methylaminopurine, 6-dimethylaminopurine, 6-mercaptopurine.

This transglycosylation method is useful for the preparation of nucleosides, nucleosides analogs, and particularly active pharmaceutical ingredients (API); comprising, containing, or consisting of nucleoside moieties, or analogs thereof. Understanding API as any substance or mixture of substances intended to be used in the manufacture of drug (medicinal) product and that, when used in the production of a drug, becomes an active ingredient of the drug product. Such substances are intended to furnish pharmacological activity or other effect in the diagnosis, cure, mitigation, treatment, or prevention of disease or to affect the structure and function of the body. (Eudralex, Part II of volume 4 EU Guidelines to Good Manufacturing Practice).

The combination of uridine phosphorylase (UPase, E.C. 2.4.2.3) and purine nucleoside phosphorylase (PNP; E.C. 2.4.2.1) efficiently transfers a sugar moiety from a donor nucleoside to an acceptor base.

When pyrimidine nucleosides are prepared departing from other pyrimidine nucleosides and pyrimidine bases as starting materials, then the use of the UPase alone is sufficient, but the use of both enzymes PNPase and UPase is preferred because the PNPase can also contribute to the phosphorolysis step. Conversely, when purine nucleosides are prepared departing from other purine nucleosides and purine bases as starting materials, then the use of both PNPase and UPase is also preferred. On the other hand, the use of both enzymes PNPase and Upase is much more successful when the reaction is from a pyrimidine to a purine nucleoside, for instance from a uridine to a 2,6 diaminopurine riboside, when compared to the use of each type of enzyme per separate.

Preferably the transglycosylation method uses a combination of the UPase and PNPase. The crude cell lysates or the clarified crude enzyme solutions may be mixed in different proportions in order to obtain an optimized biocatalyst for a particular transglycosylation reaction.

In one embodiment, in the transglycosylation method of the present invention, the UPase of *Aeropyrum pernix* and the PNPase of *Sulfolobus solfataricus* are provided by a host cell according to any one of the embodiments presented hereinbefore and hereinafter.

In one embodiment, in the transglycosylation method of the present invention, the UPase, the PNPase, or a combination thereof, are used in the form of a lysate.

In one embodiment, the transglycosylation method comprises the steps of: (i) culturing the host cell in a suitable culture medium; (ii) overexpressing the UPase, PNPase, or both; (iii) optionally preparing a cell lysate; (iv) adding a sugar-donating nucleoside, an acceptor base, and phosphate ions, and (v) recovering nucleosides from the reaction mixture.

In a particular embodiment the *Escherichia coli* transformant comprising the vector may be grown in a culture medium comprising tryptone, yeast extract, sodium chloride and an antibiotic selected from the group consisting of kanamycin, tetracycline, carbenicillin, and ampicillin, preferably at 37° C., to an optical density between 0.5-0.8 at a wavelength of approximately 600 nm. The culture may be then added with isopropyl-beta-D-thiogalactopyranoside (IPTG) to a final concentration of 100 mg/l and the inductions may be done at 37° C. between 6-12 h. Cells may be harvested by centrifugation at 4° C. and cell pellets may be lysed by three freeze-thaw cycles. The recombinant host cells may be disrupted by standard techniques known to those skilled in the art. The resulting cell lysate may be directly used as biocatalyst or centrifuged to remove cell debris and to obtain a clarified crude enzyme solutions. As used herein, the term "biocatalyst" refers to any biological entity capable of catalyzing the conversion of a substrate into a product, in this case the nucleoside biotransformation.

In one embodiment, in the transglycosylation method of the present invention, the sugar-donating nucleoside is selected from natural or modified nucleosides containing D-ribose and 2'-deoxyribose; nucleosides containing the ribose group modified in the 2', 3' and/or 5' positions; and nucleosides in which the sugar is beta-D-arabinose, alpha-L-xylose, 3'-deoxyribose, 3',5'-dideoxyribose, 2',3'-dideoxyribose, 5'-deoxyribose, 2',5'-dideoxyribose, 2'-amino-2'-deoxyribose, 3'-amino-3'-deoxyribose, 2'-fluoro-2'-deoxyribose.

In one embodiment, in the transglycosylation method of the present invention, the acceptor base is selected from natural or substituted pyrimidine and purine bases; purine bases substituted at the 1, 2, 6 positions, or a combination thereof of the purine ring; pyrimidine bases substituted at the 3, 5 positions, or a combination thereof of the pyrimidine ring; for instance purine, 2-azapurine, 8-azapurine, 1-deazapurine (imidazopyridine), 3-deazapurine, 7-deazapurine, 2,6-diaminopurine, 5-fluorouracil, 5-trifluoromethyluracil, trans-zeatin, 2-chloro-6-methylaminopurine, 6-dimethylaminopurine, 6-mercaptopurine.

In one embodiment, in the transglycosylation method of the present invention, the resulting nucleoside analogue is an active pharmaceutical ingredient (API) as known in the art.

In one embodiment, in the transglycosylation method of the present invention, said method is carried out between 60 and 100° C.

In one embodiment, the transglycosylation method of the present invention is carried out in aqueous media, or in an aprotic polar co-solvent system.

In one embodiment, the aprotic polar co-solvent system is selected from dimethylsulfoxide, tetrahydrofuran, 2-methyltetrahydrofuran, dimethylformamide, or any combination thereof.

In one embodiment, in the transglycosylation method of the present invention, the sugar-donating nucleoside is selected from uridine and 2'-deoxyuridine, and the acceptor base is 2,6-diaminopurine.

In one embodiment, the present invention provides a one-pot enzymatic synthesis of nucleosides using uridine or 2'-deoxyuridine as donors of sugar moiety, because the recombinant UPase enzyme of the present invention is most specific for these substrates. Nevertheless, this enzyme can be used with any donor of sugar moieties because it does not discriminate between uridine, 2'-deoxyuridine, and other pyrimidine nucleosides, as unfortunately occurs in many lower organisms, such as *B. stearothermophilus* [14].

In one embodiment, in the transglycosylation method of the present invention, the sugar-donating nucleoside is selected from uridine and 2'-deoxyuridine, and the acceptor base is 5-fluorouracil.

In one embodiment, in the transglycosylation method of the present invention, the sugar-donating nucleoside is selected from uridine and 2'-deoxyuridine, and the acceptor base is 5-trifluoromethyluracil.

In one embodiment, in the transglycosylation method of the present invention, the sugar-donating nucleoside is selected from uridine and 2'-deoxyuridine, and the acceptor base is trans-zeatin.

In one embodiment, in the transglycosylation method of the present invention, the sugar-donating nucleoside is selected from uridine and 2'-deoxyuridine, and the acceptor base is 2-chloro-6-methylaminopurine.

In one embodiment, in the transglycosylation method of the present invention, the sugar-donating nucleoside is selected from uridine and 2'-deoxyuridine, and the acceptor base is 6-dimethylaminopurine.

In one embodiment, in the transglycosylation method of the present invention, the sugar-donating nucleoside is selected from uridine and 2'-deoxyuridine, and the acceptor base is 6-mercaptopurine.

The term "thermostable nucleoside phosphorylase" refers to enzymes that are stable to heat, are heat resistant, and retain sufficient nucleoside phosphorylase activity to effect another reactions and does not become irreversibly denatured (inactivated) when subjected to elevated temperatures for the time necessary to effect the transglycosylation reactions.

The purpose of the Examples given below is to illustrate the present invention without constituting a limitation of the field of application thereof.

EXAMPLES

As stated above, the transglycosylation reactions according to the invention were carried out using UPase and PNPase enzymes obtained from UPase- or PNPase-producing cells. Such cells are preferably cells of genetically modified *Escherichia coli*, capable of expressing considerable quantities of UPase or PNPase. The manner of obtaining such cells, the enzymes and their characteristics, as well as the production of some nucleoside analogues are given in the accompanying examples, which are set out below.

Example 1

Construction of the *Escherichia coli* deoD

The Purine Nucleoside Phosphorylase (PNPase) of *Sulfolobus solfataricus* sequence was found in GenBank, with the accession number AE006766. The gene was amplified by PCR, using 2 units of Platinum Pfx enzyme (Invitrogen), 1 mM $MgSO_4$ and 1× enzyme amplification buffer, 200 µM dNTPs and 0.3 µM of each primer, with the oligonucleotides 5'-caccgtgccattttagaaaatggttcc-3' (*Sulfolobus solfataricus* deoD forward; SEQ ID NO. 1) and 5'-aatcagttttaagaatcttaag-gtaat-3' (*Sulfolobus solfataricus* deoD reverse; SEQ ID NO. 2) from the *Sulfolobus solfataricus* P2 [15]. The PCR reaction was performed with an initial denaturation step at 94° C. for 30 min, followed by 36 temperature cycles of a denaturation step at 94° C. for 1 min, and an annealing/extension step at 60° C. for 1.5 min and 68° C. for 1 min. After the 36 cycles, the sample was subjected to 68° C. for 10 min and finally at 4° C. PCR product was analyzed by agarose gel electrophoresis, and the DNA band was purified from the gel (S.N.A.P.™ UV-Free Gel Purification Kit, Invitrogen). The amplified fragment was cloned into the polylinker region of the pUC18 vector that carries the ampicillin resistance gene [17]. The cloned region was completely sequenced and it was found to be completely identical to the data bank sequence.

Example 2

Construction of the *Escherichia coli* Udp

The Pyrimidine Nucleoside Phosphorylase (UPase) of *Aeropyrum pernix* sequence was found in GenBank with the accession number NC_000854.2. The gene was amplified by PCR, using 2 units of Platinum Pfx enzyme (Invitrogen), 1 mM $MgSO_4$ and 1× enzyme amplification buffer, 200 µM dNTPs and 0.3 µM of each primer, with the oligonucleotides 5'-caccgtggcccgctacgttctcctc-3' (*Aeropyrum pernix* udp forward; SEQ ID NO. 3) and 5'-gaattcctatgtgcgtctgcacgccagg-3' (*Aeropyrum pernix* reverse; SEQ ID NO. 4) from the *Aeropyrum pernix* K1 [16]. The PCR reaction was performed with an initial denaturation step at 94° C. for 30 min, followed by 36 temperature cycles of a denaturation step at 94° C. for 1 min, and an annealing/extension step at 60° C. for 1.5 min and 68° C. for 1 min. After the 36 cycles, the sample was subjected to 68° C. for 10 min and finally at 4° C. PCR product was analyzed by agarose gel electrophoresis, and the DNA band was purified from the gel (S.N.A.P.™ UV-Free Gel Purification Kit, Invitrogen). The amplified fragment was cloned into the polylinker region of the pUC 18 vector that carries the ampicillin resistance gene [17]. The cloned region was completely sequenced and it was found to be completely identical to the data hank sequence.

Example 3

Cloning into pET102/D-TOPO® Vector and Cells Transformation

Figure 3:
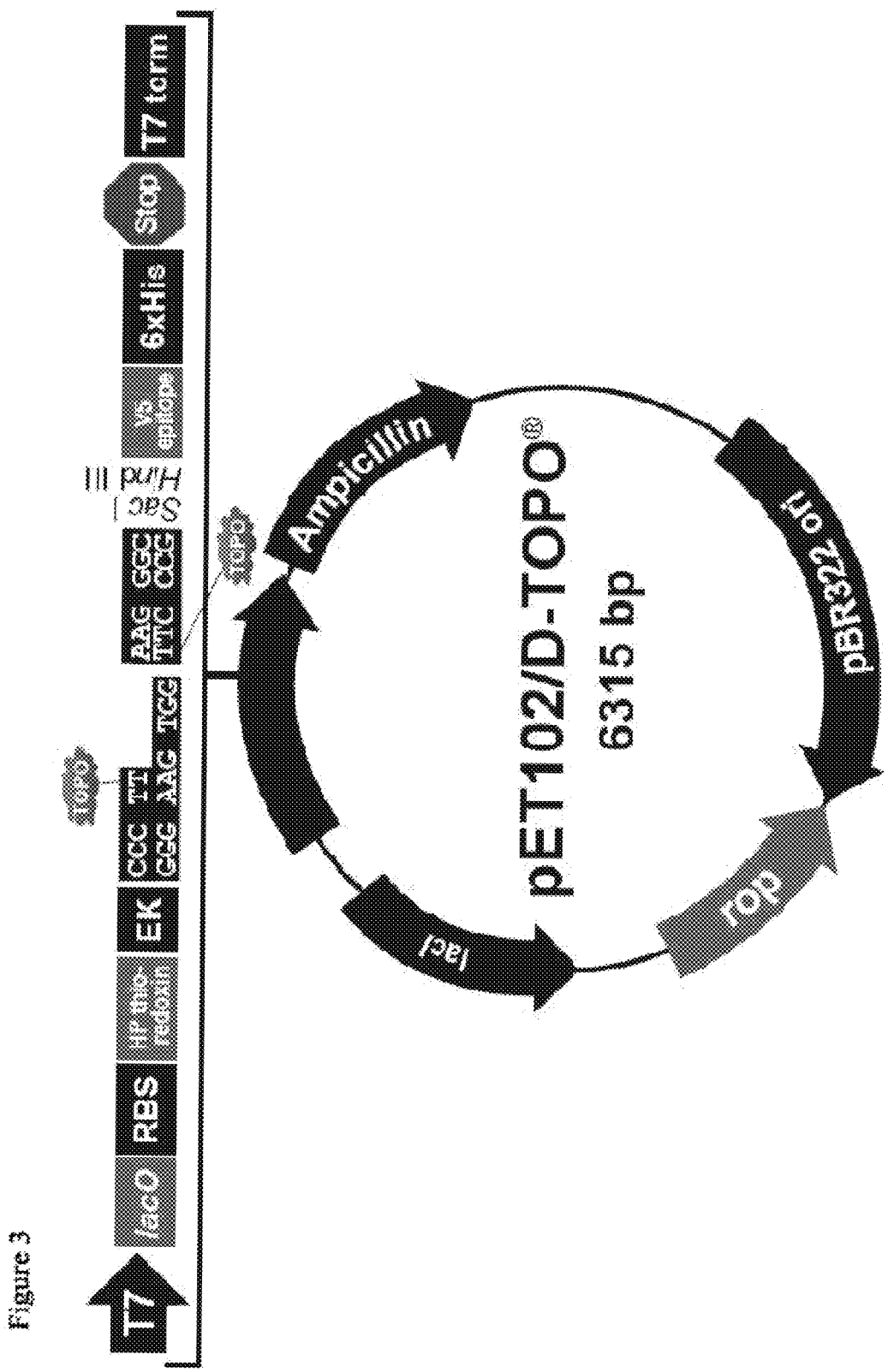
FIG. 3 shows a genetic map of the initial expression vector pET102/D-TOPO® before cloning. Vector length of 6315 nucleotides. T7 promoter: bases 209-225; T7 promoter priming site: bases 209-228; lac operator (lacO): bases 228-252; ribosome binding site (RBS): bases 282-288; His-patch (HP) thioredoxin ORF: bases 298-627; TrxFus forward priming site: bases 607-624; EK recognition site: bases 643-657; TOPO® recognition site 1: bases 670-674; overhang: bases 675-678; TOPO® recognition site 2: bases 679-683; V5 epitope: bases 700-741; polyhistidine (6×His) region: bases 751-768; T7 reverse priming site: bases 822-841; T7 transcription termination region: bases 783-911; bla promoter: bases 1407-1505; Ampicillin (bla) resistance gene (ORF): bases 1506-2366; pBR322 origin: bases 2511-3184; ROP ORF: bases 3552-3743 (complementary strand); lacI ORF: bases 5055-6146 (complementary strand).

The DNA fragments containing the *Aeropyrum pernix* udp gene sequence and *Sulfolobus sulfactaricus* deoD gene sequence were cloned into pET102/D-TOPO® vector (pET102 Directional TOPO® Expression Kit, Invitrogen) that comprises a pBR322ori for plasmid replication, ampicillin resistance gene, T7 promoter that permits binding of T7 RNA polymerase, lac operator that permits inhibition of expression when isopropylthiogalactopyranoside (IPTG) is not present, a ribosome binding site for translation of RNA, a His-patch-thioredoxin for increasing the solubility of the fusion protein, and a polyhistidine tag (6×His) for detection and purification of the fusion protein (FIG. 3). The vector was introduced by thermal shock into *Escherichia coli* BL21 (pET102 Directional TOPO® Expression Kit, Invitrogen), a commercial strain that is used for regulated expression of heterologous genes. It comprises the gene encoding the T7 RNA polymerase, which makes the strain compatible with the use of pET vectors comprising T7 promoter for the overexpression of recombinant proteins with IPTG.

The resulting recombinant vectors were analyzed by DNA restriction with 10 units of the enzyme HindIII. The positive clone was sequenced using the sequencing primers TrxFus forward 5'TTCCTCGACGCTAACCTG3' (SEQ ID NO. 5) and T7 reverse 5'TAGTTATTGCTCAGGGGTGG3' (SEQ ID NO. 6).

Example 4

Fermentation of the Recombinant Strains

The recombinant strains to which the present invention relates were cultivated separately in batch mode, at pH=7, in trypticase soy solid medium supplemented with ampicillin.

One colony of the culture was passed into nutrient broth n° 2 (Oxoid) containing Lab-lemco powder 10 g/l, peptone 10 g/l and NaCl 5 g/l, supplemented with 200 mg/l ampicillin. It was incubated at 37° C. with vigorous shaking (200 rpm). Escherichia coli strains harbouring the expression plasmid were grown to Optical Density at 600 nm of 0.6, then IPTG (up to 100 mg/l) was added and the culturing was continued for an additional 8 h. When fermentation was complete, the culture medium was centrifuged, the cell pellet was washed in 30 mM-pH 7 phosphate buffer. The biomass obtained was stored at −20° C. until it was brought into use.

Example 5

Partial UPase and PNPase Purification (Cell Lysate Preparation)

For a partial purification of the protein, cell paste, separated by centrifugation or by microfiltration from a culture of the recombinant strain that expresses the enzyme UPase or PNPase, was disrupted by the addition of 160 mg lysozyme and one hour of incubation at 0° C. followed by three ultra rapid freezing-thawing cycles (−80° C./37° C.) and a final step for reducing viscosity adding 1,000 units of deoxyribonuclease 1.

Example 6

Determination of the Enzymatic Activity of the UPase Enzyme

One hundred microliters of centrifuged cell lysate, comprising a suspension of UPase expressing cells, diluted 1:100 (volume/volume) in potassium phosphate buffer at pH 7.0, was added to 800 microliters of 75 mM uridine solution in 100 mM phosphate buffer at pH 7.0, preincubated at 30° C. After 5 minutes, the phosphorolysis reaction was stopped by addition of 1 ml of 2N HCl. An aliquot of the reaction mixture was analyzed using a high performance liquid chromatograph (HPLC), equipped with a Kromasil 100-5C18 (Akzo Nobel) column, with a size of 250×4.6 mm. The elution was carried out using a 4% methanol-water solution. The enzymatic activity of the cell lysate was expressed as units per ml ($\mu$moles of uracil$\times$min$^{-1}\times$ml$^{-1}$) and was calculated relative to a standard uracil solution eluted in the same conditions. Approximately 590 units per ml of centrifuged cell lysate were recovered.

Example 7

Determination of the Enzymatic Activity of the PNPase Enzyme

One hundred microliters of centrifuged cell lysate, comprising a suspension of PNPase expressing cells, diluted 1:100 (volume/volume) in potassium phosphate buffer at pH 7.0, was added to 800 microliters of 60 mM inosine solution in 100 mM phosphate buffer at pH 7.0, preincubated at 30° C. Exactly 10 minutes later, the phosphorolysis reaction was stopped by addition of 1 ml of 2N HCl. An aliquot of the reaction mixture was analyzed using a high performance liquid chromatography (HPLC), equipped with a Kromasil 100-5C18 (Akzo Nobel) column, with a size of 250×4.6 mm. The elution was carried out using a 4% methanol-water solution. The enzymatic activity of the cell lysate was expressed as units per ml ($\mu$moles of hypoxanthine$\times$min$^{-1}\times$ml$^{-1}$) and was calculated relative to a standard hypoxanthine solution eluted in the same conditions. Approximately 310 units per ml of centrifuged cell lysate were recovered.

Example 8

Determination of Transglycosylation Catalytic Activity

For the determination of transglycosylation catalytic activity the mixture of cell lysates containing both UPase and PNPase were prepared by mixing the lysates so as to have UPase:PNPase enzymatic-activity ratio of about 1:1, determined as in Examples 6 and 7. Transglycosylation reaction was carried out at analytical scale in the following conditions: 250 µl of cell lysates (equivalent to 14 units of each UPase and PNPase enzymatic activities) was added to 10 ml of a solution having the following composition: 4 mM 1-β-D-ribofuranosyluracil (uridine nucleoside), 4 mM adenine base, 30 mM potassium phosphate buffer pH7, thermostatically controlled at 60° C. After 1.5 hours at 60° C., the reaction was stopped by diluting the mixture 1:5 and cooling in ice. The percentage of bioconversion of adenine base to 9-β-D-ribofuranosyladenine (adenosine nucleoside) was determined by analyzing an aliquot of the reaction mixture by high performance liquid chromatography (HPLC) with the use of Kromasil 100-5C18 (Akzo Nobel) column of a size of 250×4.6 mm and eluted with a 4% methanol-water solution. The transglycosylation catalytic activity was expressed as units·ml$^{-1}$ ($\mu$moles of Ara-A formed in 1.5 hours·ml$^{-1}$ of mixture of cell lysates) or in units·g$^{-1}$ of moist resin ($\mu$moles of D-ribofuranosyladenine formed in 1.5 hours·ml$^{-1}$ of cell lysate) and was calculated relative to a standard D-ribofuranosyladenine solution eluted by HPLC in the same conditions. Under these conditions, about 55 percent of adenosine nucleoside was formed (approximately 9 units per ml of cell lysate).

Example 9

Effect of Temperature and pH on the Nucleoside Phosphorylases Activities

Figure 4:
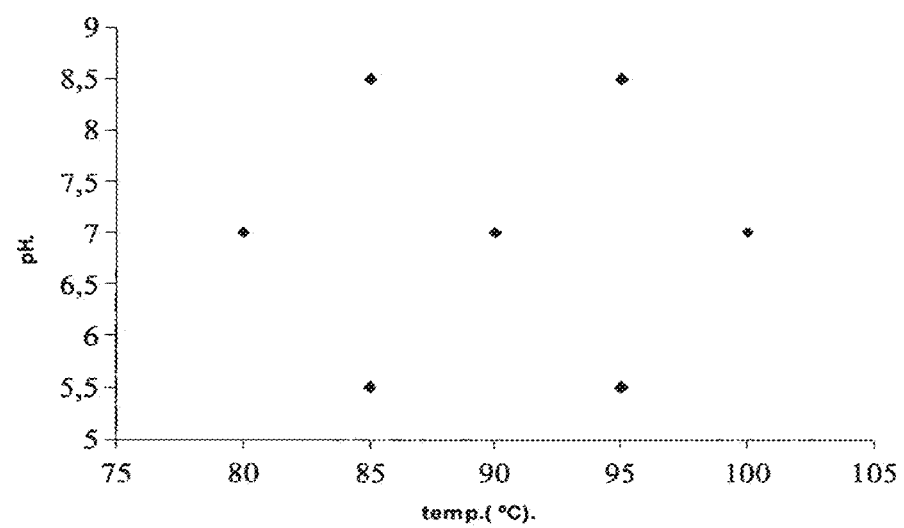
FIG. 4 depicts a "Doehlert Matrix" where five temperatures were combined with three pH values, resulting in seven combinations of temperature and pH.
Figure 5:
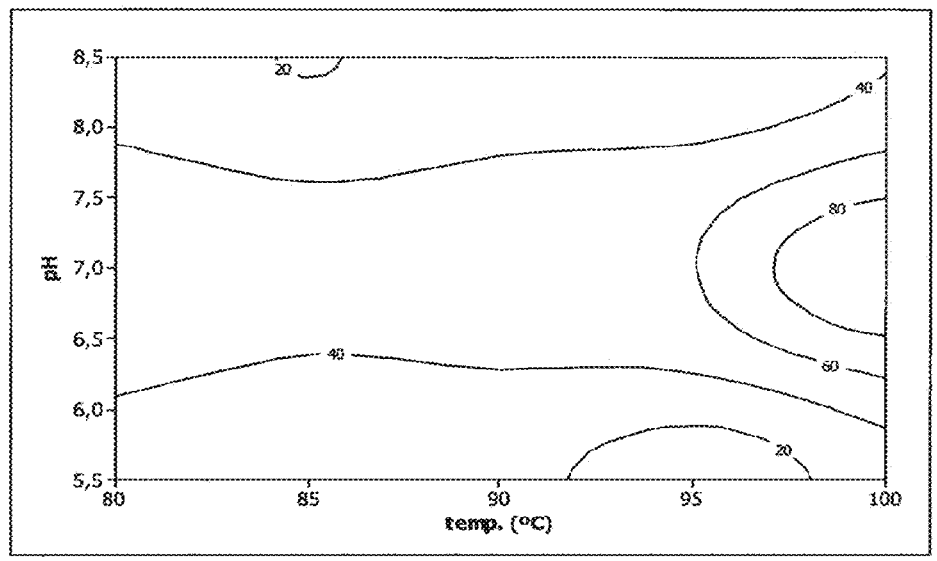
FIG. 5. Contour plot showing the interactive effect of pH and temperature on the UPase activity. Data was statistically analyzed with the Response Surface Methodology (RSM), using the "Minitab" software. The enzyme appears highly thermophilic; its activity increased sharply up to the maximal assayed temperature (100° C.) and the activity displayed a distinct pH optimum around the neutrality (6.5-7.5), preferably 7.0.
Figure 6:
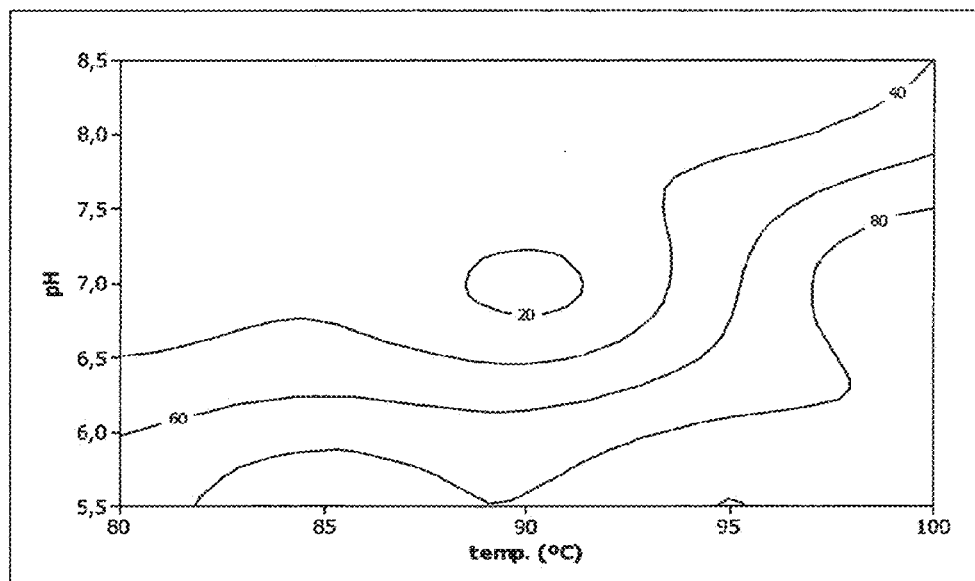
FIG. 6. Contour plot showing the interactive effect of pH and temperature on the PNPase activity. Data was statistically analyzed with the Response Surface Methodology (RSM), using the "Minitab" software. The enzyme appears highly thermophilic; its activity increased sharply up to the maximal assayed temperature (100° C.) and the activity displayed a distinct pH optimum around the neutrality (6.5-7.0).

The influence of pH and temperature on the performance of the nucleoside phosphorylases was investigated by using a "design of experiments method". Different temperatures were combined with different pH values to ascertain the conditions that resulted in maximum enzymatic activities. An experimental domain was defined between 80° C.-100° C. and pH 5.5-8.5. As shown in FIG. 4, five temperatures were combined with three pH values according to the "Doehlert Matrix", resulting in seven combinations of temperature and pH. The substrates were incubated in the selected reaction solution and temperature without enzyme, and then the enzyme was added and incubated at selected conditions. The samples were processed as described above for the determination of the enzymatic activity of the PNPase or UPase enzymes. Activity values were expressed as a percentage of the corresponding maximal values found (100%). The results are shown in FIGS. 5 and 6, respectively.

Example 10

Thermostability

Thermostability of the enzymes was assayed at 80° C. Aliquots of the enzyme were prepared, between 100 and 200 microliters of a suspension of UPase or/and PNPase expressing cells (cell lysate), diluted 1:100 or 1:1000 volume/volume in potassium phosphate buffer at pH 7.0-7.2. The biocatalysts were incubated at 80° C. for different times. After heating, the solutions were immediately kept on ice and the measuring of the nucleoside phosphorylases activities was performed as described in examples 6 and 7. No loss of nucleoside phosphorylases activities was observed after 10 h at 80° C.

Solvent Effects on Nucleoside Phosphorylase Activity

Organic co-solvents are commonly used in reactions and isolated enzymes must be able to survive under conditions of relatively high concentrations of co-solvent. Experiments were run in the presence of organic solvents such as methanol (protic polar solvent) and dimethylsulfoxide (aprotic polar solvent). The nucleoside phosphorylase enzymes of the present invention were resistant to organic solvents, exhibiting activity in a buffer solution containing 5 and 10% by volume of the organic solvent.

TABLE 1

Stability of PNPase enzyme against some organic solvents.

| Organic solvents | Relative activity (%)[a] | |
|---|---|---|
| | DMSO | MeOH |
| 5% (v/v) | 94 | 95 |
| 10% (v/v) | 115 | 86 |

[a]The relative activity of cell lysate comprising PNPase enzyme was determined using the standard assay described in example 7 at two concentrations of organic solvents and its relative activity was compared with the activity of the cell lysate comprising PNPase enzyme but no organic solvent. DMSO: dimethylsulfoxide; MeOH: methanol.

TABLE 2

Stability of UPase enzyme against some organic solvents.

| Organic solvents | Relative activity (%)[a] | |
|---|---|---|
| | DMSO | MeOH |
| 5% (v/v) | 91 | 151 |
| 10% (v/v) | 70 | 206 |

[b]The relative activity of cell lysate comprising UPase enzyme was measured using the standard assay described in example 6 at two concentrations of organic solvents and its relative activity was compared with the activity of the cell lysate comprising UPase enzyme but no organic solvent. DMSO: dimethylsulfoxide; MeOH: methanol Example 11

General Bioconversion Procedures

One-pot transglycosylation reactions were performed at selected reaction temperatures and pHs, in reaction vessels with gentle stirring. Catalytic transglycosylation activity of cell lysate mixture used was about 12 units per ml (as determined in Example 8). Nucleosides were prepared using a mixture of the cell lysate prepared to obtain a PNPase:UPase activity ratio of 1:1.

Substrates were:
1) natural 2'-deoxyribonucleosides or ribonucleosides, which act as 2'-deoxyribose-1-phosphate or ribose-1-phosphate donors;
2) a secondary natural or synthetic purine or pyrimidine base, which is linked to the position 1 of the sugar.

At the end of the reactions, the reaction mixture was centrifuged and then filtered using an Amicon Ultrafiltration device (YM-3 membrane) and the products were separated, according to the protocol provided by the manufacturer. The biocatalysts can be recycled for consecutive reactions (typically between 3-5 times) by addition of newly prepared reaction mixtures. The filtered solutions were monitorized by high performance liquid chromatography (HPLC) in the same conditions described above. Bioconversion yields were calculated based on the initial concentration of base analogue.

Example 12

Preparation of 2,6-Diaminopurine Nucleosides

The preparation of purine nucleosides is more difficult because of the low solubility of these bases in aqueous medium. In the present invention, the inventors used the enzyme competitive properties to solve this problem. The strategy used by the inventors encompasses the use of organic co-solvents and/or high temperatures to increase the solubility of the substrates.

12.1 Preparation of 2,6-Diaminopurine Nucleosides Using Co-Solvents

Assays were performed in 5 and 10% of aprotic dipolar co-solvents, at 60° C., twelve units/ml cell lysate were added to 150 ml of a solution kept thermostatically at 60° C., and having the following composition of substrate solutions:
1. 15 mM Uridine/2'-Deoxyuridine,
2. 5 mM 2,6-Diaminopurine, and
3. 30 mM potassium phosphate buffer, pH 7.

After 5 hours, the reaction mixture was filtered by centrifugation at 2000×g for 30 min, at 4° C., through an Amicon ultra-4 Centrifugal Filter Devices (Millipore, Bedford, Mass.) with a 3000-Da cutoff, and the filtrate was recovered. In table 3, the production yields of 2,6-Diaminopurine nucleosides prepared in the presence of co-solvents is shown. The resulting 2,6-Diaminopurine nucleosides (2,6-Diaminopurine riboside or 2,6-Diaminopurine deoxyriboside) were analyzed by HPLC. In these reactions, the products were obtained in high yields (over 80%).

TABLE 3

Production yields of 2,6-Diaminopurine nucleosides using different % co-solvent at 60° C.

| Co-solvent | Substrate | Analog base | Product | Yield (%) |
|---|---|---|---|---|
| 10% DMSO | Uridine | 2,6-Diaminopurine | 2,6-Diaminopurine riboside | 97 |
| 10% DMSO | 2'-Deoxyuridine | 2,6-Diaminopurine | 2,6-Diaminopurine deoxyriboside | 96 |
| 5% THF | Uridine | 2,6-Diaminopurine | 2,6-Diaminopurine riboside | 84 |
| 5% THF | 2'-Deoxyuridine | 2,6-Diaminopurine | 2,6-Diaminopurine deoxyriboside | 90 |

THF: Tetrahydrofuran; DMSO: dimethylsulfoxide 12.2. Preparation of 2,6-Diaminopurine Nucleosides Without the Use of Co-Solvents The preparation of 2,6-Diaminopurine nucleosides without co-solvents could only be carried out at temperatures above 80° C. due to limited water solubility of this purinic base. Assays were performed at different temperatures (80, 90 and 100° C.). Twelve units/ml cell lysate were added to 150 ml of a solution kept thermostatically at the selected temperature, and having the following composition of substrate solutions:
1. 15 mM Uridine/2'-Deoxyuridine,
2. 5 mM 2,6-Diaminopurine, and
3. 30 mM potassium phosphate buffer, pH 7.

After 5 hours, the reaction mixture was filtered by centrifugation at 2000×g for 30 min, at 4° C., through an Amicon ultra-4 Centrifugal Filter Devices (Millipore, Bedford, Mass.) with a 3000-Da cutoff, and the filtrate was recovered. In table 3, the production yields of 2,6-Diaminopurine nucleosides prepared in the presence of co-solvents is shown. The resulting 2,6-Diaminopurine nucleosides (2,6-Diaminopurine riboside or 2,6-Diaminopurine deoxyriboside) were analyzed by HPLC. In table 4, the production yields of 2,6-Diaminopurine nucleosides prepared without organic solvents are shown. The bioconversion yield of the reaction was around 80% in all temperatures assayed.

TABLE 4

Production yields of 2,6-Diaminopurine nucleosides at different temperatures without use organic co-solvents.

| | Temperature (° C.) | | |
| --- | --- | --- | --- |
| | 80 | 90 | 100 |
| Biotransformation (%) | 79.3 | 79.6 | 81.1 |

Example 13

Preparation of Other Nucleosides

Transglycosylation reactions were carried out using various acceptor bases. The reactions were carried out at 80° C. for various periods of time with 10% of DMSO as co-solvent for purinic base and without co-solvent use for pyrimidinic aceptor bases. The percentage of bioconversion was calculated relative to the initial concentration of acceptor base and was determined by HPLC analysis of the reaction mixture.

13.1 Preparation of Trifluoromethyluracil Nucleosides

One ml catalyst (cell lysate) with transglycosylation activity of about 12 units/ml cell lysate were added to 150 ml of a solution kept thermostatically between 80° C., and having the following composition:
7.5 mM uridine/2'-Deoxyuridine,
2.5 mM Trifluoromethyluracil, and
20 mM potassium phosphate buffer, pH 7.

After 3 hour at 80° C., the reaction mixture was filtered by centrifugation at 2000×g for 30 min, at 4° C., through an Amicon ultra-4 Centrifugal Filter Devices (Millipore, Bedford, Mass.) with a 3000-Da cut-off, and the filtrate was recovered. The bioconversion yield of the reaction was higher than 60%. The resulting trifluoromethyluracil nucleosides (trifluoromethyluridine or 7'-deoxytrifluoromethyluridine) were analyzed by HPLC.

13.2 Preparation of 5-Fluoruracil Nucleosides

5-Fluoruracil nucleosides were prepared as previously described above. One ml catalyst (cell lysate) with transglycosylation activity of about 12 units/ml cell lysate was added to 150 ml of a solution kept thermostatically at 80° C. and having the following composition:
7.5 mM uridine/2'-Deoxyuridine,
2.5 mM 5-fluorouracil, and
30 mM potassium phosphate buffer, pH 7.

After 3 hour at 80° C., the reaction mixture was filtered by centrifugation at 2000×g for 30 min, at 4° C., through an Amicon ultra-4 Centrifugal Filter Devices (Millipore, Bedford, Mass.) with a 3000-Da cut-off, and the filtrate was recovered. The bioconversion yield of the reaction was higher than 50%. The resulting 5-fluoruracil nucleosides (5-fluorouridine and 5-fluoro-2'-deoxyuridine) were analyzed by HPLC.

13.3 Preparation of trans-Zeatin Nucleosides trans-Zeatin nucleosides were prepared as described above. One ml catalyst (cell lysate) with transglycosylation activity of about 12 units/ml cell lysate was added to 150 ml of a solution kept thermostatically at 80° C. and having the following composition:
7.5 mM Uridine/2'-Deoxyuridine,
2.5 mM trans-Zeatin, and
30 mM potassium phosphate buffer, pH 7.

The assays were performed in 10% (v/v) DMSO as co-solvent using the conditions described above. After 5 hours at 80° C., the reaction mixture was filtered by centrifugation at 2000×g for 30 min, at 4° C., through an Amicon ultra-4 Centrifugal Filter Devices (Millipore, Bedford, Mass.) with a 3000-Da cut-off, and the filtrate was recovered. The bioconversion yield of the reaction was higher than 80%. The resulting trans-zeatin nucleosides (trans-zeatin riboside and trans-zeatin deoxyriboside) were analyzed by HPLC.

13.4 Preparation Process for 2-Chloro-6-methylaminopurine Nucleosides

2-Chloro-6-methylaminopurine nucleosides were prepared as described before. One ml catalyst (cell lysate) with transglycosylation activity of about 12 units/ml cell lysate were added to 150 ml of a solution kept thermostatically at 80° C. and having the following composition:
15 mM Uridine/2'-Deoxyuridine,
5 mM 2-Chloro-6-Methylaminopurine, and
30 mM potassium phosphate buffer, pH 7.

The assays were performed in 10% (v/v) DMSO as co-solvent using the conditions described above. After 5 hours at 80° C., the reaction mixture was filtered by centrifugation at 2000×g for 30 min, at 4° C., through an Amicon ultra-4 Centrifugal Filter Devices (Millipore, Bedford, Mass.) with a 3000-Da cut-off, and the filtrate was recovered. The bioconversion yield of the reaction was higher than 80%. The resulting 2-chloro-6-methylaminopurine nucleosides (2-chloro-6-methylaminopurine riboside and 2-chloro-6-methylaminopurine deoxyriboside) were analyzed by HPLC.

13.5 Preparation of 6-Dimethylaminopurine Nucleosides

6-Dimethylaminopurine nucleosides were prepared as described above. One ml catalyst (cell lysate) with transglycosylation activity of about 12 units/ml cell lysate was added to 150 ml of a solution kept thermostatically at 80° C. and having the following composition:
15 mM Uridine/2'-Deoxyuridine,
5 mM 6-Dimethylaminopurine, and
30 mM potassium phosphate buffer, pH 7.

The assays were performed in 10% (v/v) DMSO as co-solvent using the conditions described above. After 5 hours at 80° C., the reaction mixture was filtered by centrifugation at 2000×g for 30 min, at 4° C., through an Amicon ultra-4 Centrifugal Filter Devices (Millipore, Bedford, Mass.) with a 3000-Da cut-off, and the filtrate was recovered. The bioconversion yield of the reaction was higher than 80%. The resulting 6-dimethylaminopurine nucleosides (6-dimethylaminopurine riboside and 6-dimethylaminopurine deoxyriboside) were analyzed by HPLC.

13.6 Preparation of 6-Mercaptopurine Nucleosides

6-Mercaptopurine nucleosides were prepared as described above. One ml catalyst (cell lysate) with transglycosylation activity of about 12 units/ml cell lysate was added to 150 ml of a solution kept thermostatically at 80° C. and having the following composition:
15 mM Uridine/2'-Deoxyuridine,
5 mM 6-Mercaptopurine, and
30 mM potassium phosphate buffer, pH 7.

The assays were performed in 10% (v/v) of DMSO as co-solvent using the conditions described above. After 5 hours at 80° C., the reaction mixture was filtered by centrifugation at 2000×g for 30 min, at 4° C., through an Amicon ultra-4 Centrifugal Filter Devices (Millipore, Bedford, Mass.) with a 3000-Da cut-off, and the filtrate was recovered. The bioconversion yield of the reaction was higher than 50%. The resulting 6-mercaptopurine nucleosides (6-mercaptopurine riboside and 6-mercaptopurine deoxyriboside) were analyzed by HPLC.

All publications, patents, and patent applications cited in this document are incorporated by reference herein in their entirety, as though individually incorporated by reference.

REFERENCES

1. Van Rompay A, Johansson M, & Karlsson A (2003) Substrate specificity and phosphorylation of antiviral and anticancer nucleoside analogues by human deoxyribonucleoside kinases and ribonucleoside kinases. (Translated from eng) *Pharmacol Ther* 100(2):119-139 (in eng).
2. Yu X, Li G., Qi X, & Deng Y (2005) Stereoselective synthesis of 9-beta-d-arabianofuranosyl guanine and 2-amino-9-(beta-d-arabianofuranosyl)purine. (Translated from eng) *Bioorg Med Chem Lett* 15(3):683-685 (in eng).
3. Hutchinson, Trends Biotechnol. 8, 348-353, 1990
4. EP 1141328, Keryos Spa
5. Taran S A, Verevkina. K N, Esikova. T Z, Feofanov S A, & Miroshnikov A I (2008) [Synthesis of 2-chloro-2'-deoxyadenosine by microbiological transglycosylation using a recombinant *Escherichia coli* strain]. (Translated from rus) *Prikl Biokhim Mikrobiol* 44(2):181-186 (in rus).
6. Cacciapuoti G, et al. (2009) Purine nucleoside phosphorylases from hyperthermophilic Archaea require a CXC motif for stability and folding. *FEBS J* 276(20):5799-5805
7. Cacciapuoti G, et al. (2005) A novel hyperthermostable 5'-deoxy-5'-methylthioadenosine phosphorylase from the archaeon *Sulfolobus solfataricus*. (Translated from eng) *FEBS J* 272(8):1886-1899 (in eng).
8. Cacciapuoti G, et al. (2007) Biochemical and structural characterization of mammalian-like purine nucleoside phosphorylase from the Archaeon *Pyrococcus furiosus*. (Translated from eng) *FEBS J* 274(10):2482-2495 (in eng).
9. Brown, S. H. and Kelly, R. M. (1993) Characterization of Amylolytic Enzymes, Having Both alpha-1,4 and alpha-1,6 Hydrolytic Activity, from the Thermophilic Archaea *Pyrococcus furiosus* and *Thermococcus litoralis*. *Appl Environ Microbiol* 59, 2614-2621.
10. Fujiwara, S., Lee, S. G., Haruki, M., Kanaya, S., Takagi, M. and Imanaka, T. (996) Unusual enzyme characteristics of aspartyl-tRNA synthetase from hyperthermophile archaeon *Pyrococcus* sp. KOD1. *FEBS Lett* 394, 66-70.
11. Purcarca, C., Simon, V., Pricur, D. and Hervé, G. (1996) Purification and characterization of carbamoyl-phosphate synthetase from the deep-sea hyperthermophilic archaebacterium *Pyrococcus abyssi*. *Eur J Biochem* 236, 189-199.
12. Cacciapuoti, G., Fusco, S., Caiazzo, N., Zappia, V. and Porcelli, M. (1999) Heterologous expression of 5'-methylthioadenosine phosphorylase from the archacon *Sulfolobus solfataricus*: characterization of the recombinant protein and involvement of disulfide bonds in thermophilicity and thermostability. *Protein Expr Purif* 16, 125-135.
13. Bzowska A, Kulikowska E, & Shugar D (2000) Purine nucleoside phosphorylases: properties, functions, and clinical aspects. (Translated from eng) *Pharmacol Ther* 88(3):349-425 (in eng).
14. Saunders, P. P., Wilson, B. A. and Saunders, G. F. (1969) Purification and comparative properties of a pyrimidine nucleoside phosphorylase from *Bacillus stearothermophilus*. *J Biol Chem* 244, 3691-3697.
15. She Q, et al. (2001) The complete genome of the crenarchaeon *Sulfolobus solfataricus* P2. (Translated from eng) *Proc Natl Acad Sci USA* 98(14):7835-7840 (in eng).
16. Kawarabayasi Y, et al. (1999) Complete genome sequence of an aerobic hyperthermophilic crenarchaeon, *Aeropyrum pernix* K1. (Translated from eng) *DNA Res* 6(2):83-101, 145-152 (in eng).
17. Yanisch-Perron C, et al. (1985) Improved M13 phage cloning vectors and host strains: nucleotide sequences of the M13 mp18 and pUC19 vectors. Gene. 33(1):103-19

The invention claimed is:

1. A recombinant expression vector comprising:

the sequence encoding a uridine phosphorylase (UPase, EC. 2.4.2.3);

said sequence operably linked to one or more control sequences that direct the production of said phosphorylase in a suitable expression host;

said sequence originating from the Archaea Thermoprotei class, wherein the UPase is from *Aeropyrum pernix* (SEQ ID No. 8).

2. A host cell comprising the recombinant expression vector according to claim 1.

3. The host cell according to claim 2, wherein said host cell is *Escherichia coli*.

4. The host cell according to claim 2, wherein the host cell is in the form of a lysate.

* * * * *

SEQUENCE LISTING

```
<160> NUMBER OF SEQ ID NOS: 8

<210> SEQ ID NO 1
<211> LENGTH: 28
<212> TYPE: DNA
<213> ORGANISM: artificial
<220> FEATURE:
<223> OTHER INFORMATION: primer related to Sulfolobus solfataricus deoD
      forward

<400> SEQUENCE: 1
```

```
caccgtgcca tttttagaaa atggttcc                                          28

<210> SEQ ID NO 2
<211> LENGTH: 27
<212> TYPE: DNA
<213> ORGANISM: artificial
<220> FEATURE:
<223> OTHER INFORMATION: primer related to Sulfolobus solfataricus deoD
      reverse

<400> SEQUENCE: 2
aatcagtttt aagaatctta aggtaat                                           27

<210> SEQ ID NO 3
<211> LENGTH: 25
<212> TYPE: DNA
<213> ORGANISM: artificial
<220> FEATURE:
<223> OTHER INFORMATION: primer related to Aeropyrum pernix udp forward

<400> SEQUENCE: 3
caccgtggcc cgctacgttc tcctc                                             25

<210> SEQ ID NO 4
<211> LENGTH: 28
<212> TYPE: DNA
<213> ORGANISM: artificial
<220> FEATURE:
<223> OTHER INFORMATION: primer related to Aeropyrum pernix udp reverse

<400> SEQUENCE: 4
gaattcctat gtgcgtctgc acgccagg                                          28

<210> SEQ ID NO 5
<211> LENGTH: 18
<212> TYPE: DNA
<213> ORGANISM: artificial
<220> FEATURE:
<223> OTHER INFORMATION: primer related to TrxFus forward

<400> SEQUENCE: 5
ttcctcgacg ctaacctg                                                     18

<210> SEQ ID NO 6
<211> LENGTH: 20
<212> TYPE: DNA
<213> ORGANISM: Artificial
<220> FEATURE:
<223> OTHER INFORMATION: primer related to T7 reverse

<400> SEQUENCE: 6
tagttattgc tcagggtgg                                                    20

<210> SEQ ID NO 7
<211> LENGTH: 825
<212> TYPE: DNA
<213> ORGANISM: Sulfolobus solfataricus

<400> SEQUENCE: 7
gtgccatttt tagaaaatgg ttccatggta tatggtgatt tcattagaaa tcaagaggta        60
agaaaaagaa ttacaaagga agaacttggg atagaagaag acgaaatccc ggaaagggta       120
gttgtaacac ctatgccatt taatactcaa tttcctaaaa actttgaaga tactttaact       180
aacttaggaa ttaaagtaaa taggttaaaa gtggaagacc aaatacttag acaattcgga       240
ggaaatttat tgcttgaaaa agacggtaat agaggattta ttgcgttcat aggcagaggt       300
```

```
ctgatagatt tcactgagag gataaggatt ttagctacag tttcgcgcat taaagatata    360
ttatttattg gtactgcagg atcgttatct aatgaaatat taataggaga tctaaatata    420
ccaaaatacg ccatcccatt cgaaaacgta agtgattttt acgctgatcc taccatagca    480
attccacaag ctgatgaaaa gttgctgaac gaagtttatg agtacgctga ggaaactgga    540
gttaaaaccc actcaacctt acatgcaaca ctacttttcc cttattccga aactactgag    600
ttcctaaact acttattaaa tatcggcgtt tctacgatag atatggaagt cagtgctttt    660
tataagatgt ctagatttta cggtaaaaga gctgttgcag tattacgaat ttcagatatg    720 ccttttaatag aactgcataa gcaagaggaa ttgattaagg caagaaggga aattgcagtt    780
aatgctgttt tcagaattac cttaagattc ttaaaactga tttaa                   825

<210> SEQ ID NO 8
<211> LENGTH: 765
<212> TYPE: DNA
<213> ORGANISM: Aeropyrum pernix

<400> SEQUENCE: 8
gtggcccgct acgttctcct cccgggagac cccgagagga cagaccttat agcccgcctc     60
tgggatgaag cgaggcttgt agcgcaccac cgggagtaca ggacgtggac cggcttctac    120
aaggggacat cgataagtgt aacaagcacc gggataggct ctcccagcac ggcgatagcc    180
gttgaggagc tgctgagggt tggagccgag actttcataa gagtaggcac tatgggcggt    240
ataagggagg atctgcggcc cggcaccctg gttataggga gtgcggcggt taggatggag    300
gggacgagcg gccagtacgc tccccggggg ttcccagcgg ccgccagcta tgacgttgtg    360
gcggcgctgg tggaggctgc tgaggcgctc ggggttaggt atgaggttgg cgttgttgcc    420
agcacggaca gcttctacct gggccagggg aggccggggt acgggggta tatgacgccg    480 gaggcttcgg aagtcatacc cctcctcagg tcagccggcg tcctcggctt cgagatggag    540
gcctccgccc tcttcacccct atcccagctc tacggcgcca gggcagggtg cgtgtgcgcg    600
gtagtggcaa acaggggttag cggggagttt gtggtaaacg cggggggttga agacgctgct    660 agggttgcct ccgaggcggt agccatacta gcaggctggg acaggagag ggagaagagg    720 ggtaagaaat ggttttaccc gagcctggcg tgcagacgca catag                   765
```